(12) United States Patent
Boele et al.

(10) Patent No.: US 12,653,444 B2
(45) Date of Patent: Jun. 16, 2026

(54) SYSTEM AND METHOD FOR REMOTE NEUROBEHAVIORAL TESTING

(71) Applicant: The Trustees of Princeton University, Princeton, NJ (US)

(72) Inventors: Henk-Jan Boele, Hopewell, NJ (US); Samuel S.-H. Wang, Princeton, NJ (US)

(73) Assignee: THE TRUSTEES OF PRINCETON UNIVERSITY, Princeton, NJ (US)

( * ) Notice: Subject to any disclaimer, the term of this patent is extended or adjusted under 35 U.S.C. 154(b) by 412 days.

(21) Appl. No.: 18/036,009

(22) PCT Filed: Nov. 10, 2021

(86) PCT No.: PCT/US2021/058698
§ 371 (c)(1),
(2) Date: May 9, 2023

(87) PCT Pub. No.: WO2022/103784
PCT Pub. Date: May 19, 2022

(65) Prior Publication Data
US 2023/0404464 A1     Dec. 21, 2023

Related U.S. Application Data

(60) Provisional application No. 63/218,607, filed on Jul. 6, 2021, provisional application No. 63/197,002, filed on Jun. 4, 2021, provisional application No. 63/111,960, filed on Nov. 10, 2020.

(51) Int. Cl.
*A61B 5/11*      (2006.01)
*A61B 5/00*      (2006.01)

(52) U.S. Cl.
CPC .......... *A61B 5/4041* (2013.01); *A61B 5/1103* (2013.01)

(58) Field of Classification Search
CPC ........................... A61B 5/4041; A61B 5/1103
See application file for complete search history.

(56) References Cited

U.S. PATENT DOCUMENTS

| | | |
|---|---|---|
| 2007/0090603 A1 | 4/2007 | Miletich |
| 2012/0097012 A1 | 4/2012 | Kurihara et al. |
| 2012/0274906 A1* | 11/2012 | Privitera .............. A61B 3/0083 |
| | | 351/246 |
| 2014/0088341 A1 | 3/2014 | Altman et al. |

(Continued)

FOREIGN PATENT DOCUMENTS

| | | |
|---|---|---|
| JP | 2003018942 A | 1/2003 |
| JP | 2017176641 A | 10/2017 |

OTHER PUBLICATIONS

KR Office Action corresponding to KR App No. 2023-7018839, dated Oct. 14, 2025 and English Translation.

(Continued)

*Primary Examiner* — Daniel L Cerioni
(74) *Attorney, Agent, or Firm* — Meagher Emanuel Laks Goldberg & Liao, LLP

(57) ABSTRACT

A system and method for neurobehavioral testing, including eyeblink conditioning and prepulse inhibition, without air puffs, that utilizes an electronic device with a light source, a camera, and a speaker, and makes assessments based on the degree to which an eyelid is closed after a user is exposed to conditional and unconditional stimuli.

12 Claims, 5 Drawing Sheets

(56)            References Cited

U.S. PATENT DOCUMENTS

| | | |
|---|---|---|
| 2016/0022135 A1 | 1/2016 | Agarwal et al. |
| 2016/0073874 A1 | 3/2016 | Tsai et al. |
| 2016/0082259 A1 | 3/2016 | McCabe et al. |
| 2016/0171324 A1 | 6/2016 | Ionita |
| 2019/0008435 A1 | 1/2019 | Cakmak |
| 2020/0100719 A1 | 4/2020 | Cakmak |

OTHER PUBLICATIONS

JP Office Action corresponding to JP App No. 2023-528017, dated Feb. 10, 2025 and English Language Translation.

Yasuji Kishimoto, "Blink Reflex Conditioning," Brain Science Dictionary, May 5, 2016, (https://bsd.neuroinf.jp/wiki/); DOI: 10.14931/bsd.6400.

English Translation of Japanese Office Action for corresponding JP Application No. 2023-528017, dated May 28, 2025.

Boele, H.J. et al., "Accessible and reliable neurometric testing in humans using a smartphone platform," medRxiv, https://doi.org/10.1101/2023.02.01.23285291, Feb. 2, 2023.

Boele, Henk-Jan et al., "Cerebellar and extracerebellar involvement in mouse eyeblink conditioning: the ACDC model," Frontiers in Cellular Neuroscience, vol. 3, Art. 19, Jan. 2010.

Bolbecker, Ph.D., Amanda R. et al., "Eye-Blink Conditioning Deficits Indicate Temporal Processing Abnormalities in Schizophrenia," Schizophrenia Research, vol. 111, Nos. 1-3, pp. 182-191, Jun. 2009.

Coesmans, MD, PhD, Michael et al., "Cerebellar motor learning deficits in medicated and medication-free men with recent-onset schizophrenia," Journal of Psychiatry & Neuroscience, vol. 39, No. 1, pp. E3-E11, 2014.

Freeman, John H. and Steinmetz, Adam B., "Neural circuitry and plasticity mechanisms underlying delay eyeblink conditioning," Learning & Memory, vol. 18, pp. 666-677, 2011.

Frings, Markus et al., "Timing of conditioned eyeblink responses is impaired in childrenwith attention-deficit/hyperactivity disorder," Experimental Brain Research, vol. 201, pp. 167-176, 2010.

Koekkoek, S.K.E. et al., "Deletion of FMR1 in Purkinje Cells Enhances Parallel Fiber LTD, Enlarges Spines, and Attenuates Cerebellar Eyelid Conditioning in Fragile X Syndrome," Neuron, vol. 47, pp. 339-352, Aug. 4, 2005.

Lubow, R.E., "Classical eyeblink conditioning and schizophrenia: A short review," Behavioural Brain Research, vol. 202, pp. 1-4, 2009.

Medina, Javier F. et al., "Parallels Between Cerebellum and Amygala-Dependent Conditioning," Nature Reviews Neuroscience, vol. 3, pp. 122-131, Feb. 2002.

Oristaglio, Jeff et al., "Children with autism spectrum disorders show abnormal conditioned response timing on delay, but not trace, eyeblink conditioning," Neuroscience, vol. 248, pp. 708-718, Sep. 17, 2013.

Parker, Krystal L. et al., "Eyeblink conditioning in unmedicated schizophrenia patients: A positron emission tomography study," Psychiatry Research, vol. 214, No. 3, pp. 402-409, Dec. 30, 2013.

Bakker, Paul et al., "Real-time face and landmark localization for eyeblink detection," arXiv:2006.00816v2, Jul. 15, 2020.

Yeo, Christopher H. Yeo and Hesslow, Germund, "Cerebellum and conditioned reflexes," Trends in Cognitive Sciences, vol. 12, No. 9, pp. 322-330, Sep. 1, 1998.

European Supplementary Search Report for corresponding PCT Application No. PCT/US2021058698, dated Jan. 1, 2025.

International Search Report and Written Opinion for corresponding PCT Application No. PCT/US2021/058698, dated Mar. 25, 2022.

European Search Report for corresponding EP 21892692; dated Dec. 13, 2024.

\* cited by examiner

*1*

*2*

*3*

*4*

*4*

*50*

*55*

*60*

*65*

*70*

*3*

*5*

*10*    *11*

*15*

*20*    *21*

*25*

*30*

*35*    *45*

*40*

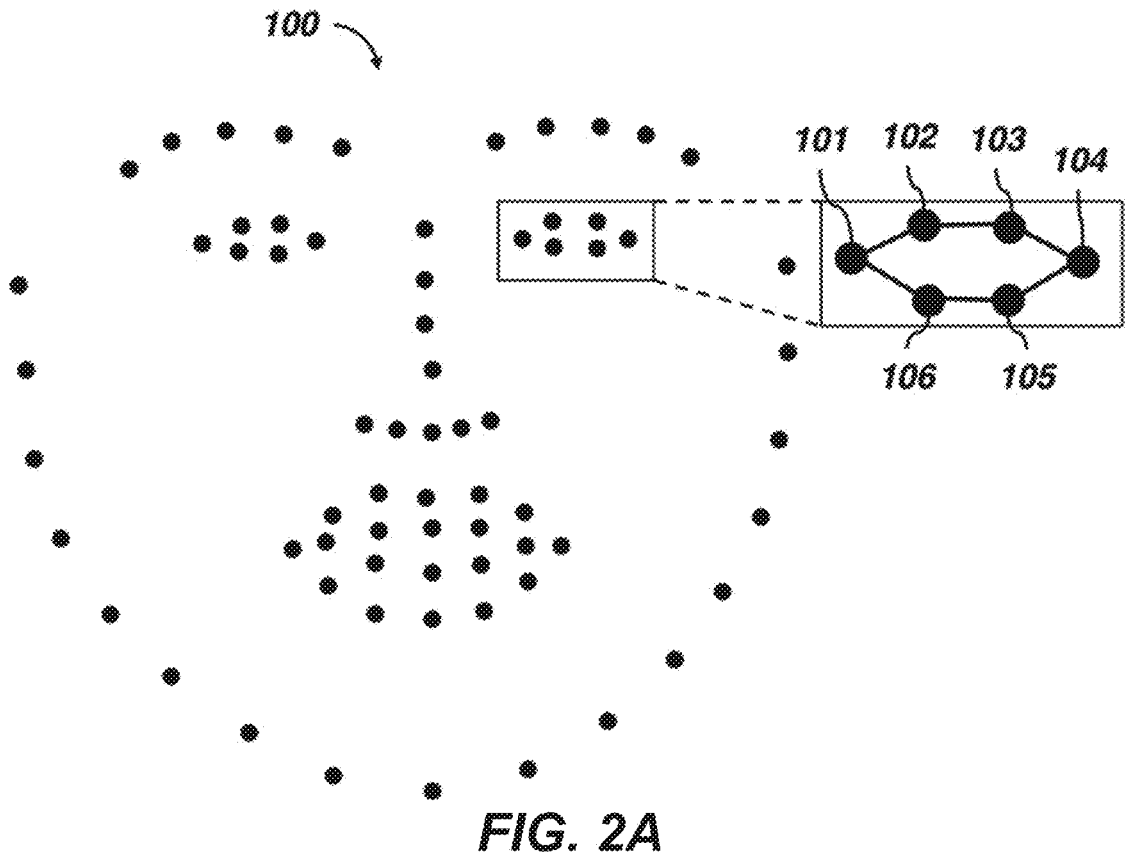
*FIG. 2A*
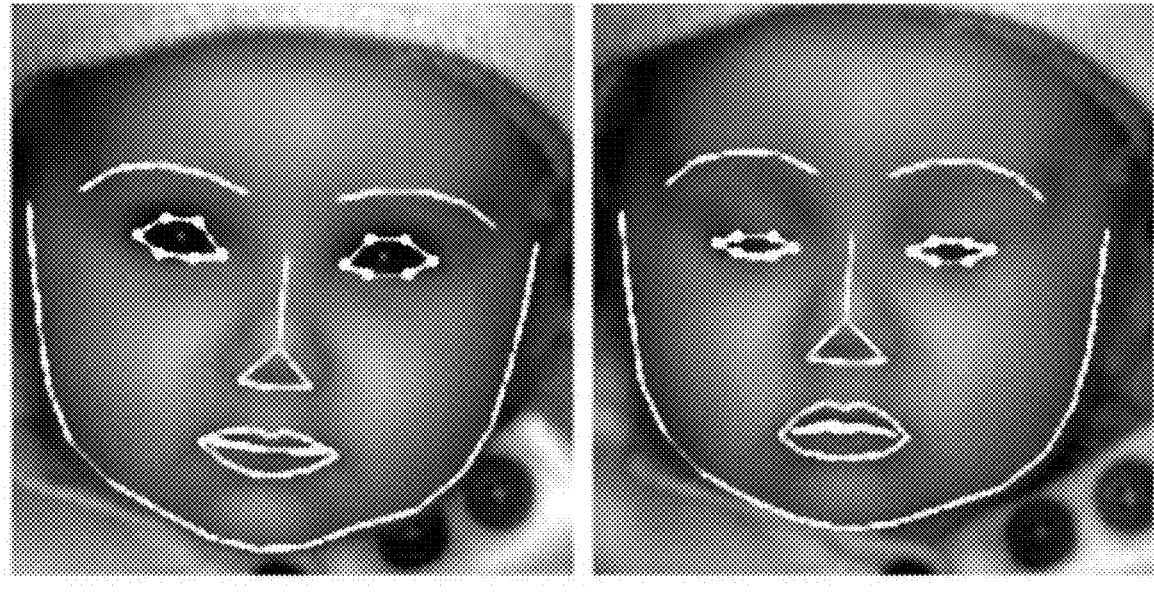
*FIG. 2B*        *FIG. 2C*

SYSTEM AND METHOD FOR REMOTE NEUROBEHAVIORAL TESTING

CROSS-REFERENCE TO RELATED APPLICATIONS

This application claims priority to U.S. Provisional Patent Application No. 63/111,960, filed Nov. 10, 2020, U.S. Provisional Patent Application No. 63/197,002, filed on Jun. 4, 2021, and 63/218,607, filed on Jul. 6, 2021, all of which are hereby incorporated in their entirety by reference.

STATEMENT REGARDING FEDERALLY SPONSORED RESEARCH OR DEVELOPMENT

This invention was made with government support under Grant #R01-NS045193 awarded by the National Institutes of Health. The government has certain rights in the invention.

BACKGROUND

To study the function and dysfunction of specific brain regions, researchers and clinicians have developed a wide range of so-called neurobehavioral tests. A neurobehavioral test can be defined as a specifically designed task to investigate the (dys)function of a certain brain structure. Two tasks that have proven to be particularly useful in psychology and neuroscience are eyeblink conditioning (EBC) and prepulse inhibition of the acoustic startle reflex (PPI). EBC is a popular variant of classical conditioning experiments performed by Ivan Pavlov and is considered as one of the best behavioral methods to specifically investigate the (dys) function of cerebellum.

During EBC experiments, subjects will hear a tone that is followed half a second later by an air puff to the eye, which will elicit a blink reflex. Because of the repeated tone-puff pairings, subjects will eventually close their eyes in response to the tone, which is called the conditioned response (CR). EBC is simple in its form, yet measures multiple aspects of how we learn in our daily life. It includes associative learning, since subjects learn to make a correct new association, and motor learning, since subjects learn an eyelid motor response with millisecond timed precision.

PPI is the behavioral phenomenon whereby the magnitude of the startle response is inhibited when a short and loud startling sound (the pulse) is preceded by a weaker sound that does not elicit a startle reflex (the prepulse). Herewith, PPI measures sensorimotor gating, which is the mechanism of the nervous system to filter out irrelevant sensory information to protect the brain from overstimulation and enabling appropriate reaction to stimuli that are relevant. PPI is less brain region specific and probes midbrain function and modulatory effects that the midbrain receives from limbic systems, thalamus, and prefrontal areas.

Eyeblink conditioning and PPI have been used for over a century and as such the neural mechanisms underlying these tasks have been clarified in high detail. In addition, it appeared that both eyeblink conditioning and PPI can be readily done in both humans and animals, making both tasks potentially valuable for translational clinical studies. Moreover, performance in both tests appear to be strongly correlated with neuropsychiatric disorders, including autism spectrum disorder (ASD), and have therefore been suggested repeatedly as potential biomarkers or even diagnostic tools. For these reasons, both tasks hold the promise that, at some point in time, they will be beneficial for patients suffering from neuropsychiatric disorders.

However, eyeblink conditioning and PPI are not yet used as translational or diagnostic instruments in daily clinical practice. Why not? First, the sensitivity and specificity of the tests for diagnosing heterogeneous neurodevelopmental and neuropsychiatric disorders is not yet characterized. Second, studies on human eyeblink conditioning and PPI are often underpowered and subject to inclusion bias, whereby one group (often psychology students who serve as 'healthy controls') are overrepresented, rendering limited value for understanding society at large. Third, eyeblink conditioning and PPI setups are rarely commercially available and often expensive. Fourth, the tasks in their current forms are unpleasant, since they often require instrumentation on the participant's face and use an aversive air puff to the eye, making it almost impossible to perform these tasks in young children and especially ASD patients. Finally, the tasks lack any form of standardization; for example, the behavior of the experimenter who performs the experiment and the emotional condition of the participant can have a profound influence on the outcome, leading to low reproducibility between labs. Fueled by the variability among patients examined in the different hospitals, clinicians are hesitant to use eyeblink conditioning and PPI in their daily practice, while at the same time, researchers continue to routinely perform eyeblink conditioning and PPI experiments in their own laboratories, which are well-controlled but often configured in a unique set of stimulus parameters.

As a result, after a century of scientific investment in eyeblink conditioning and PPI, efforts have not or very minimally been translated directly to patients. Thus, a system and method that bridge this gap between fundamental knowledge of neural processes and clinical application, with a utility that could effectively enhance diagnostics in patients with neurodevelopmental and neuropsychiatric disorders is useful and desirable.

BRIEF SUMMARY

A first aspect of the present disclosure is drawn to a method for neurobehavioral testing the includes eyeblink conditioning without air puffs. The method comprises, without requiring any equipment attached to the head or face, the following steps: (i) starting to emit a sound from a speaker on a device (preferably a mobile device, such as a smartphone); (ii) capturing one or more initial images of at least one eye while the sound is being emitted; (iii) emitting a light from a light source on the mobile device while the sound is being emitted, the emission of light beginning a fixed period of time (such as between 100 milliseconds and 1 second) after the sound began emitting; (iv) capturing one or more final images of the at least one eye while the light and sound are being emitted; (v) stopping the emission of the sound and the light; and repeating steps (i)-(v).

The method preferably also comprises determining a degree of openness of the at least one eye in each of the initial and final images. Advantageously, the method further includes transmitting the degree of openness, the initial images, and/or the final images, to a remote device or server (e.g., so a researcher or doctor can review the findings).

Preferably, the method further comprises determining a degree to which a conditioned response is acquired, based on the determined degree of openness of the at least one eye in the one or more initial images.

The method may advantageously include testing the degree to which a conditioned response has been acquired, by: (i) starting to emit a sound from a speaker on a mobile device; (ii) capturing one or more images of at least one eye while the sound is being emitted; (iii) stopping the emission of the sound; and (iv) determining a degree of openness of those captured images and determining a degree to which the conditioned response was acquired, based on the determined degree of openness of those captured images.

In some preferred embodiments, the method may comprise beginning steps a-f of the disclosed method based on a signal received from a remote device or server.

Advantageously, the method further comprises activating a vibration motor when the sound is begins being emitted, and deactivating the vibration motor when the sound stops being emitted.

A second aspect of the present disclosure is drawn to a method for neurobehavioral testing, where the testing involves detecting prepulse inhibition in a user. The method comprises emitting a white noise prepulse, where the white noise prepulse has a first strength configured to not elicit a startle reflex in the user, and then, after a delay in which no white noise is emitted, emitting a white noise pulse having a second strength configured to elicit a startle reflex in the user, the second strength being greater than the first strength. The eye blink detection as described above can be used to measure a degree of openness of an eye. By comparing to a standard, or comparing to a A third aspect of the present disclosure is drawn to a device (preferably a mobile or portable device, such as a smartphone) for eyeblink conditioning without air puffs, configured to perform the above method. The device comprises a light source (such as a camera flash, a separate LED, or a display screen), a camera, a speaker, one or more processors, optionally a wireless transceiver, and optionally a vibration-generating motor. The processors are configured with instructions that, when executed, cause the processors to perform several tasks: (a) cause the speaker configured to start emitting a sound at a first point in time; (b) cause the light source configured to start emitting light at a second point in time that follows the first point in time after a fixed delay interval (such as a time between 100 milliseconds and 1 second) (e.g., beginning to emit light a fixed period of time after the sound began emitting); (c) stop emitting the sound and stop emitting the light at the third point in time; (d) receive one or more first images of at least one eye from the camera while the speaker is emitting a sound and the light source is not emitting light; (e) receive one or more second images of the at least one eye from the camera while the speaker is emitting a sound and the light source is emitting light; and (f) determine a degree of openness of the at least one eye in each of the one or more first images and each of the one or more second images.

In some embodiments, the processors are further configured to transmit (e.g., via the wireless transceiver) the degree of openness to a remote device or server, and/or transmit the one or more first images, the one or more second images, or a combination thereof, to a remote device or server.

Advantageously, in some embodiments, the processor is further configured to determine a degree to which a conditioned response is acquired, based on the determined degree of openness of the at least one eye in the one or more first images.

Advantageously, in some embodiments, the vibration motor is configured to start vibrating at the first point in time and stop vibrating at the third point in time.

In some embodiments, the device comprises a display screen, and the display screen is configured to display a video or image, an augmented reality video or image, or a virtual reality video or image during the testing process.

Advantageously, the one or more processors are further configured to cause prepulse inhibition, by causing a white noise prepulse to be emitted, and after a delay period, causing a white noise pulse to be emitted, where a strength of the pulse is greater than a strength of the prepulse.

BRIEF DESCRIPTION OF DRAWINGS

FIG. 2A is an image of a template for tracking facial landmarks, and eye landmarks in particular.

FIG. 2B is an image of a baby with eyes open, with an overlay of a template tracking eyelid positioning.

FIG. 2C is an image of a baby with eyes closed, with an overlay of a template tracking eyelid positioning.

DETAILED DESCRIPTION

Figures 1A, 1B, 1C:
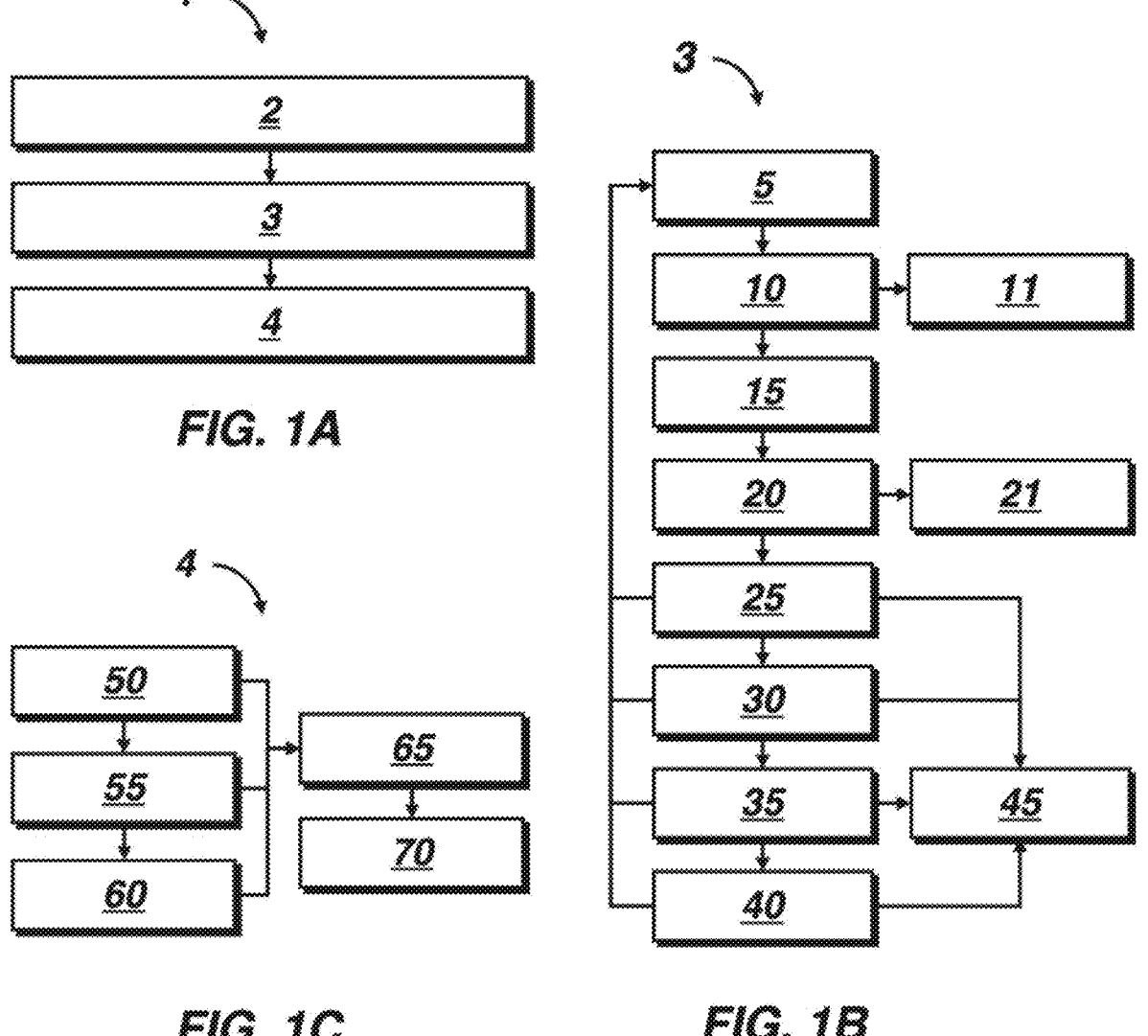
FIG. 1A is a simplified flowchart of an embodiment of a method for neurobehavioral testing.
FIG. 1B is a simplified flowchart of an embodiment of steps for eyeblink conditioning without an air puff.
FIG. 1C is a simplified flowchart of an embodiment of steps for testing prepulse inhibition.

Embodiments of the present disclosure are described in detail with reference to the figures wherein like reference numerals identify similar or identical elements. It is to be understood that the disclosed embodiments are merely examples of the disclosure, which may be embodied in various forms. Well known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

The disclosed method for neurobehavioral testing, which may comprise, e.g., eyeblink conditioning or prepulse inhibition, can be described with reference to FIGS. 1A, 1B, and 1C.

In FIG. 1A, the method 1 for neurobehavioral testing can generally be understood as requiring at least one of testing for eyeblink conditioning without air puffs 3, testing prepulse inhibition 4, or a combination thereof. If both are tested, the order of testing does not matter—that is, the prepulse inhibition testing can be done prior to eyeblink conditioning, or vice-versa.

In some embodiments, the testing also includes a calibration sequence 2, where a plurality of images of the subject are captured, at least one of which is with eyes fully open and at least one of which is with the eyes fully closed. In some embodiments, this is done by capturing a short video sequence (such as 30 seconds), after which each image in the video sequence is then analyzed as described below in order to determine the maximum and minimum degree the eyelids are open.

Eyeblink Conditioning

In FIG. 1B, an embodiment of a method for eyeblink conditioning without air puffs 3 is shown. The method will generally require a user to have access to a device, preferably a mobile or portable device, and most preferably a smartphone or tablet. The device will generally require a camera, a light source, and a speaker, and optionally a vibrational motor and/or a wireless transceiver. No equipment is (or needs to be) attached to the face and/or head of the user. In some embodiments, the device may be in contact with the user's face or head during use, but is not attached (e.g., while the device may be placed into contact with the user's face, such as placed in front of their eyes, the user can pull their face away from the device without needing assistance or using their hands, etc.). In some embodiments, the device is not in contact with the user's face or head during use.

The method 3 generally begins by starting to emit a sound 5 from the speaker on the device. This is the conditional stimulus. In some embodiments, the user initiates the start of the method 3. In a preferred embodiment, a remote device or server is used to send a signal to the device, and based on the signal, the method 3 begins.

In some preferred embodiments, in addition to emitting a sound, a vibration motor is activated in the device, causing the user to experience the vibrations at the same time the sound is emitted.

While the sound is being emitted, and the user is facing the camera, the camera is used to capture 10 one or more initial images of at least one eye of the user. In preferred embodiments, both eyes are captured. In some embodiments, only a single eye is captured.

In some embodiment, the camera captures the one or more initial images as video. In some embodiments, the camera captures the one or more initial images as discrete photos captured at a set frequency (such as ever 50 milliseconds, every 100 milliseconds, or every 200 milliseconds).

Optionally the captured one or more initial images is stored 11 on a non-transitory computer readable storage medium. In some embodiments, the non-transitory computer readable storage medium is on the device. In some embodiments, the device sends the images to a remote device or server in order for storage in a database.

After the sound begins emitting, a delay occurs for a fixed period of time. After the delay, a light is emitted 15 from the light source, towards the user's eyes, while the sound is still being emitted. The delay is preferably for 1 second or less, and more preferably for a period of time between 100 milliseconds and 1 second. In some embodiments, this period of time can be set or adjusted by a remote device or server. For example, in some embodiments, a doctor or researcher can adjust the period of time before the method 3 starts to account for differences in subjects, etc.

For the light flash, the color may be any color, although preferably white is used, and any color temperature may be used (such as 2800K to 5500K). When using a display screen as the light source, preferably, the maximum brightness capable of being produced by the phone is used for the emitted light 15.

The light is preferably a camera flash or similar relatively short burst of intense white or substantially white bright light from an LED or similar source of light. This includes alternative approaches, such as, e.g., displaying a full white screen on a smartphone at the brightest intensity for a short period of time. In some embodiments, the light source is configured to output a light of at least 2,500 lumens. In some embodiments, the light source is configured to emit this light for less than 1 second, preferably less than $\frac{1}{10}$ of a second, and more preferably for less than $\frac{1}{100}$ of a second.

While the sound and light are being emitted, and the user facing the camera, the camera is used to capture 20 one or more final images of the at least one eye of the user. In preferred embodiments, both eyes are captured. In some embodiments, only a single eye is captured.

In some embodiment, the camera captures the one or more final images as video. In some embodiments, the camera captures the one or more final images as discrete photos captured at a set frequency (such as ever 50 milliseconds, every 100 milliseconds, or every 200 milliseconds).

Optionally the captured one or more final images is stored 21 on a non-transitory computer readable storage medium. In some embodiments, the non-transitory computer readable storage medium is on the device. In some embodiments, the device sends the images to a remote device or server in order for storage in a database.

After the final images are captured, the emission of sound and light (and the vibration motor, if used) is stopped 25.

Generally, the above steps (5-25) are repeated at least once, and preferably a plurality of times, and more preferably at least five times.

At any time after the at least one initial image is captured 10, the method preferably comprises determining 30 a degree of openness of the at least one eye in each captured image.

Preferably, computer vision and image processing techniques are used to detect fully automated and real-time landmarks on the human face. More preferably, the algorithm is optimized to provide fast and accurate tracking of eyelids in both adults and infants. Any appropriate technique known to train a machine-learning algorithm can be utilized here.

In preferred embodiments, the algorithm is used to detect a plurality of landmarks on the face. In FIG. 2A, an example of a template 100, using 68 landmarks, is shown. In preferred embodiments, the template 100 comprises or consists of 6 landmarks for each eye captured in the image. The six landmarks are, as seen in FIG. 2A, a left corner 101, an upper left eyelid mark 102, an upper right eyelid mark 103, a right corner 104, a bottom right eyelid mark 105, and a bottom left eyelid mark 106.

Once the landmarks are identified, calculations can be made.

Specifically, for each image, a Fraction Eyelid Closure (FEC) can be calculated. Using the preferred six landmarks as an example, conceptually, the calculation is made by looking at the differences in position of the six marks, and in particular:

$$FEC = \frac{(\|\text{Upper Left } 102 - \text{Lower Left } 106\| + \|\text{Upper Right } 103 - \text{Lower Right } 105\|)}{2 * (\|\text{Left Corner } 101 - \text{Right Corner } 104\|)}$$

When looking at multiple images of the same individual, a normalized ($FEC_{NORM}$) can be determined, based on the minimum FEC ($FEC_{MIN}$) and maximum FEC ($FEC_{MAX}$). Specifically, $FEC_{NORM} = 1 - (FEC - FEC_{MIN})/(FEC_{MAX})$. An $FEC_{NORM}$ of 0 corresponds to an eye that is fully open, and an $FEC_{NORM}$ of 1 corresponds to an eye that is fully open.

In some embodiments, where 2 eyes are detected, an FEC is calculated for each eye and the results are averaged together. In some embodiments where 2 eyes are detected, an FEC is calculated for each eye, and the minimum value is utilized. In some embodiments where 2 eyes are detected, an FEC is calculated for each eye, and the maximum value is utilized. In some embodiments where 2 eyes are detected, an FEC is calculated for each eye, a difference between the two FEC values is determined. If the difference is above a threshold, the value of a flag is set to 1 or a variable is increased, indicating an anomalous response occurred.

In some embodiments, if no eyes are detected in a given image, or more than two eyes are detected, the image is skipped.

In some embodiments, a calibration sequence 2 has occurred prior to this step, and $FEC_{MIN}$ and $FEC_{MAX}$ values are determined based the images or video captured during calibration. In preferred embodiments, $FEC_{MIN}$ and $FEC_{MAX}$ values are determined based solely on the images or video captured as part of the initial or final images discussed above.

Figure 2D:
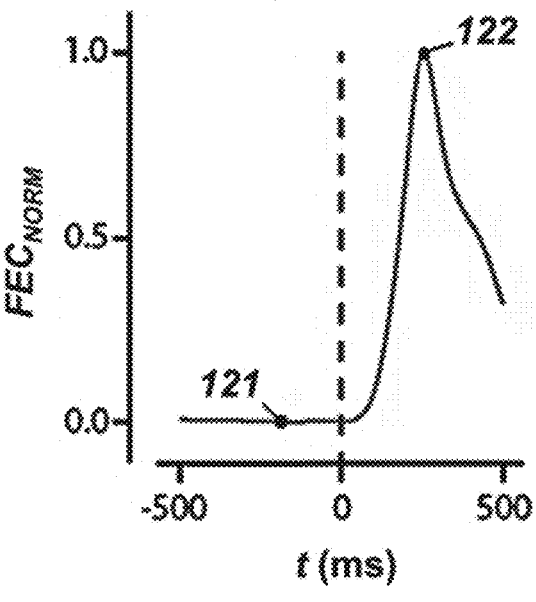
FIG. 2D is a graph showing representative normalized fractional eyelid closure ($FEC_{NORM}$) values as determined from images using the disclosed method.

Referring to FIGS. 2B and 2C, images can be seen where the landmarks have been identified around the eyes for a baby with eyes fully open (FIG. 2B) and eyes fully closed (FIG. 2C). As seen in FIG. 2D, it can be seen that by analyzing multiple images both before and after the flash occurs (in FIG. 2D, the flash occurs at time t=0), an image corresponding to $FEC_{MIN}$ 121 can be identified (here, FIG. 2B) as well as $FEX_{MAX}$ 122 (here, FIG. 2C). By looking at $FEC_{NORM}$ values in FIG. 2D, it is seen that by looking at multiple images, the openness of the eyelids can be tracked over time.

In some embodiments, the method further comprises determining a degree to which a conditioned response is acquired 35, based on the determined degree of openness of the at least one eye in the one or more initial images.

Figure 2E:
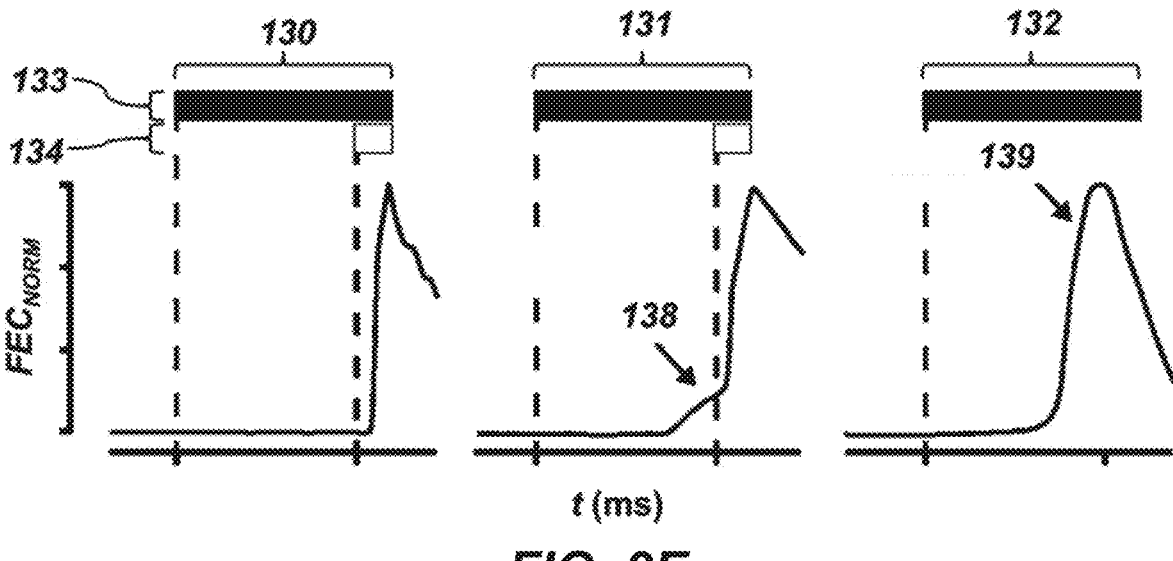
FIG. 2E is a representation of eyeblink conditioning as detected over several iterations.

The eyeblink conditioning can be seen with respect to FIG. 2E. In the first iteration 130 of the above-described steps (5-25), the tone sounds 133 at the beginning, and after a time (here, 400 ms), the light flashes 134, and soon afterwards, the eye is fully closed. Of note, prior to the light flashing, the eye is fully opened, even when the tone is being emitted. In a later iteration 131, it can be seen that the eye begins to blink (close) 138 after the sound is emitted and before the light is flashed 400 ms later. However, it still peaks at a time after the light flash starts. At this stage, some eyeblink conditioning has occurred, but it is not fully conditioned. The degree of conditioning can be determined in a variety of ways. In some embodiments, the degree is simply the maximum value of $FEC_{NORM}$ at the time the light begins flashing. In FIG. 2E, in a later iteration 131, $FEC_{NORM}$ at the time the light flash begins is roughly 0.2, so the degree of conditioning would be ~0.2, or about 20%.

In the last iteration 132, the eyeblink conditioning is complete. In FIG. 2E, the eye is closing 139 completely by the time the flash normally would have occurred. In this case, no flash occurred—only sound was emitted and the images were captured and analyzed.

In some embodiments, the method comprises a testing 40 the degree to which the conditioned response has been acquired. The last iteration 132 in FIG. 2E is representative of this testing. Specifically, it can be seen that to test the degree of conditioning, the testing may comprise first starting to emit a sound from a speaker, similar to step 5. A vibrating motor may also begin vibrating at this time. One or more images are then captured of at least one eye while the sound is being emitted, and then the emission of sound is stopped. The captured images are then analyzed as discussed above with respect to determining 30 a degree of openness of the at least one eye in each captured image.

In some embodiments, the method further comprises transmitting 45 at least some of the images or calculated values to a remote device or server. In some embodiments, this involves transmitting the determined degree of openness to a remote device or server. In some embodiments, this involves transmitting the one or more initial images, the one or more final images, or a combination thereof, to a remote device or server. In some embodiments, this involves transmitting the degree of conditioned response to a remote device or server.

In a preferred embodiment, all processing of the images to determine an openness, etc. (e.g., steps 30, 35, 40) is done on the device. In another preferred embodiment, no processing of the images to determine an openness, etc. (e.g., steps 30, 35, 40) is done on the device—all processing is done on a remote device or server.

In some embodiment, before the testing is performed, the ambient light levels are detected. For example, in some embodiments, too high of an ambient light level may decrease or eliminate a blink response. In such cases, if the ambient light level is above a given threshold, the test can be aborted, the user can be directed to move to a darker area or turn off lights, or the ambient light intensity can be used as a dependent variable when analyzing the data.

Prepulse Inhibition

As described above, the method 1 may also, or alternatively, according to claim 1, comprise testing prepulse inhibition in a user 4.

Referring to FIG. 1C, the method 4 generally comprises several steps. To test prepulse inhibition, the method optionally begins by first emitting a white noise prepulse 50, the white noise prepulse having a first strength configured to not elicit a startle reflex in the user. The lack of a startle reflex following this prepulse 50 can optionally be confirmed by capturing one or more images 65 after the prepulse is emitted, and not detecting any substantial degree of eyelid closure as described above with respect to eyeblink conditioning.

The method may then optionally include emitting a white noise pulse 55 having a second strength configured to elicit a startle reflex in the user, the second strength being greater than the first strength. The existence of a startle reflex following this pulse 55 can optionally be confirmed by capturing one or more images 65 after the pulse is emitted, and determining a first degree of eyelid closure as described above with respect to eyeblink conditioning.

The method comprises where both the prepulse and pulse are emitted with a delay between them 60. Specifically, this step comprises emitting a white noise prepulse 50, the white noise prepulse having the first strength configured to not elicit a startle reflex in the user, and then, after a delay in which no white noise is emitted, emitting a white noise pulse having the second strength configured to elicit a startle reflex in the user, the second strength being greater than the first strength.

The existence of prepulse inhibition can be confirmed following the pulse in step by capturing one or more images 65 after the pulse is emitted, then determining another degree of eyelid closure as described above with respect to eyeblink conditioning. In some cases, step 60 is sufficient. In some cases, steps 60 and 65 are sufficient. In some embodiments, the method also includes comparing 70 the degree of eyelid closure determined after just the pulse 55 was emitted to the degree of eyelid closure determined after the prepulse and pulse were emitted 60. In some embodiments, the difference between the two can be determined. In some embodiments, a ratio of the two can be determined.

Figure 2F:
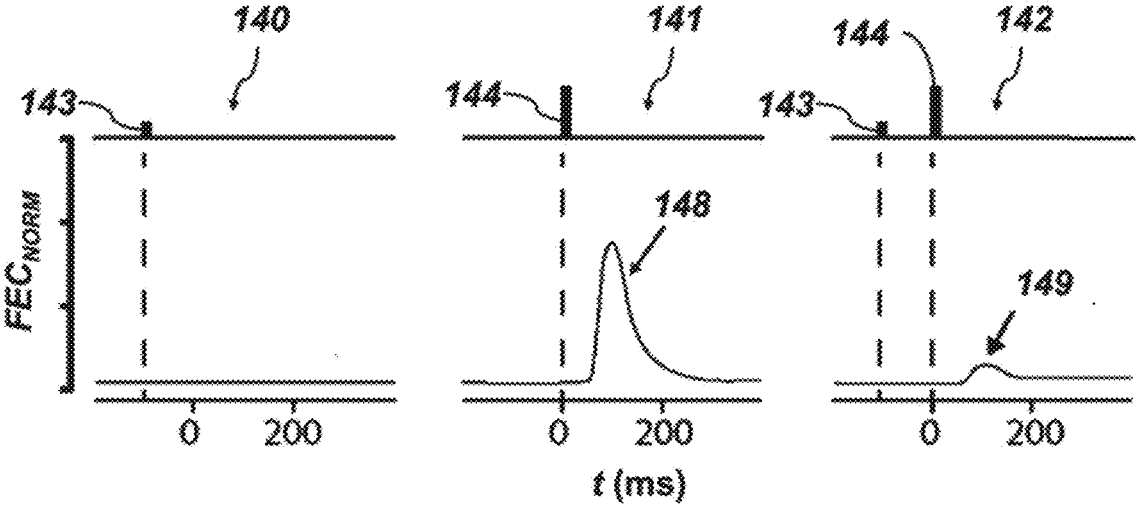
FIG. 2F is a representation of a process of testing prepulse inhibition.

As seen in FIG. 2F, the process described above is illustrated. In the first step 140, a prepulse 143 is emitted at time t<0. As seen in the graph of $FEC_{NORM}$, no eyeblink occurs. In the second step 141, a pulse 144 is emitted at time t=0. Within 200 ms, the eye has closed by a significant amount, but has not closed completely (a peak value of $FEC_{NORM}$ of ~0.67). In the third step, a prepulse 143 is emitted at time t<0, and at time t=0, a pulse 144 is emitted. As seen, prepulse inhibition has occurred—within 200 ms, the start reflex, correlated here with the degree of eye closure, is detected but has decreased significantly (a peak value of $FEC_{NORM}$ of ~0.1).

In some embodiments, the process uses a closed-loop system for measuring a user's response (e.g., blink/no blink) evoked by the white noise pulses/prepulses. If it is too loud (e.g., the prepulse causes a startle response), the process will lower the volume, and/or it is too weak (e.g., the pulse does not cause a startle response), the process will increase the volume. The volume adjustments will continue until the proper intensities have been reached.

System/Device

Figure 3:
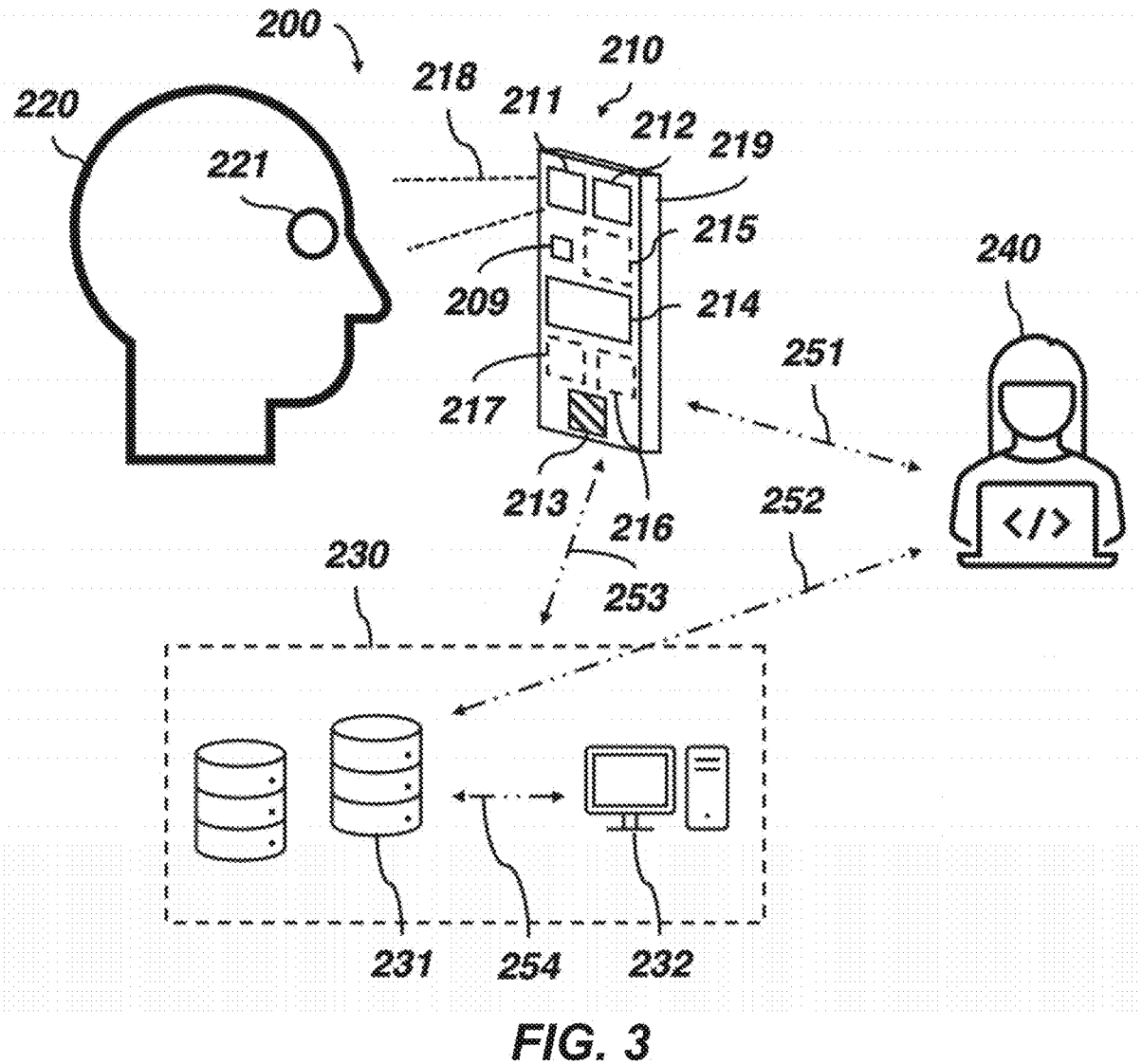
FIG. 3 is a simplified schematic of a system and device according to an embodiment of the present disclosure.

Referring to FIG. 3, embodiments of a system 200 and device 210 useful for performing the above methods can be seen. The system 200 broadly includes a device 210 that can be held and/or used by a user or participant 220, a remote location 230 the contains, e.g., one or more databases 231 that the device 210 can communicate with, and optionally a remote user 240 (such as a clinician, researcher, doctor, etc.) who can interact with the device and the user, either directly or indirectly.

Disclosed is a device 210 for neurobehavioral testing (such as eyeblink conditioning and prepulse inhibition) that does not use air puffs or require a source of a gas (such as compressed air). The device 210 generally comprises a light source 211, a camera 212, a speaker 213, one or more processors 215, an optional wireless transceiver 216 and an optional vibrational motor 217. All of the components are preferably at least partially within an outer housing 219. In some embodiments, the device 210 includes a second light source 214. In some preferred embodiments, the device 210 includes a light sensor 209.

In some embodiments, the device is a desktop or laptop computing device. The device is preferably a mobile or portable device, such as a smartphone or tablet. The one or more processors then run a program (such as an app on a smartphone) that cause the processors to perform certain instructions.

The light source can be any appropriate light source that is capable of generating a light that can cause a person to blink in normal use conditions. In one preferred embodiment, the light source is a camera flash (such as the camera flash on a smartphone), or a display screen. For example, the processor could be configured to cause the camera flash to occur, or to cause the display screen to display a plain white (or substantially white) screen at full brightness for a brief period of time. In a preferred embodiment, the device comprises both a display screen and a camera flash. In some embodiments, only a single light source is used to emit light as described previously. In other embodiments, all light sources are used to emit light as described previously.

In some embodiments, the one or more processors are configured to be connected, wired (e.g., via a USB cable) or wirelessly (e.g., via Bluetooth, to a camera and/or light source contained in a separate housing. For example, in some embodiments, a desktop computer can be connected to an appropriate device, such as a Bulbicam neuro-ophthalmic diagnostic tool from Bulbitech.

In a preferred embodiment, the device 210 includes a light sensor 209 for detecting the ambient light levels. If the ambient light level is above a threshold level, the user may be asked to move to a darker location or turn off some lights. If the ambient light level is below a different threshold level, the user may be asked to move to a brighter location, or to turn on some lights.

When the device 210 is configured to perform eyeblink conditioning as described above, the one or more processors are configured with instructions that, when executed, cause the one or more processors to: (i) cause a speaker 213 to start emitting a sound at a first point in time and stop emitting a sound at a second point in time; (ii) cause a light source 211 to start emitting light 218 towards at least one eye 221 (that is, the light being directed to illuminate the eye) of a user or participant 220 at a third point in time and stop emitting light at the second point in time, where the third point in time follows the first point in time after a fixed delay interval (such as between 100 milliseconds and 1 second); (iii) receive one or more first images of at least one eye from the camera 212 while the speaker 213 is emitting a sound and the light source is not emitting light; (iv) receive one or more second images of the at least one eye 221 from the camera 212 while the speaker 213 is emitting a sound and the light source 211 is emitting light 218. This processor may be configured to repeat the process after a delay.

Preferably, the one or more processors are also configured to determine a degree of openness of the at least one eye in each of the one or more first images and the one or more second images. This is accomplished as described previously, by using the facial detection and/or image processing software to identify landmarks on the face and the eyes, and, e.g., calculating an FEC for each image.

As described previously, in some embodiments, the device comprises a vibration motor and the processor is further configured to cause the vibration motor to start/activate vibrating at the first point in time and stop/deactivate vibrating at the second point in time (that is, to coincide with the sound being emitted).

The one or more processors may be configured to show or play on the display screen of the device a video or image, an augmented reality video or image, or a virtual reality video or image. In some embodiments, this display begins prior to the sound being emitted and may stop after the testing is over (such as when virtual or augmented reality video and objects are used for the test), or before the light is emitted from the light source (if the entire display is needed to generate a bright light).

Because this process requires capturing a participant's face and measuring unique features of the participant's brain capacities, privacy and security must be considered when determining what information is saved and where it is saved.

In a preferred embodiment, the raw images of the face never leave the device. The images are stored, for a short period of time, locally on the device (e.g., in flash memory) in order to allow the processor on the device to analyze the images and make determinations using the facial landmark detection algorithms and equations described previously. In some of these embodiments, the one or more processors are configured to, after making the determinations, provide a report of performance (e.g., on a display screen), and optionally show a comparison of the user's scores with scores of gender- and/or age-matched other users. In some of these embodiments, the users can optionally transmit 253 their scores and/or determinations to one or more databases 231 (but not the raw images) at a remote location 230, where the data would be stored anonymously. In some embodiments, the databases 231 can be managed and/or queried 254 by a computer 232 at the remote location. In other embodiments, the databases 231 can be managed and/or queried by a remote user 240 (such as a clinician, researcher, etc.).

In another preferred embodiment, such as when a trial or test is being performed, a remote user 240 (e.g., a professional user) will preferably use the application to perform neurobehavioral testing on a given number of participants or patients. The professional user will be able to control all stimulus parameters and data-acquisition parameters. In some embodiments, the device 210 directly communicates 251 with the remote user 240. However, in preferred embodiments, the device 210 communicates 253 with a remote location 230 (e.g., remote servers and one or more databases 231), and the remote user 240 communicates 252 with the remote location 230 (e.g., the same remote servers and one or more databases 231). The professional user will preferably have access to some or all of any acquired data, including raw images of faces, calculated or determined values, etc, that would typically be available during normal neurobehavioral data. Data can be easily exported to any desired platform, preferably a SQL relational database system, and analyzed using the facial landmark detection algorithms as described previously running on a normal desktop computer or CPU/GPU cluster.

Thus, in some embodiments, the one or more processors 215 are further configured to determine a degree to which a conditioned response is acquired, based on the determined degree of openness of the at least one eye in the one or more first images. This determination may then be transmitted 251, 253 to a remote device or server. In some embodiments, the one or more processors 215 are further configured to transmit 251, 253 the degree of openness to a remote device or server. In some embodiments, the one or more processors 215 are further configured to transmit 251, 253 the one or more first images, the one or more second images, or a combination thereof, to a remote device or server.

When the device 210 is configured to perform prepulse inhibition testing as described above, the one or more processors are configured with instructions that, when executed, cause the one or more processors to, at a minimum: (i) cause a white noise prepulse to be emitted, and (ii) after a delay period, cause a white noise pulse to be emitted, where a strength of the pulse is greater than a strength of the prepulse. As described previously, one or more images of one or more eyes may be captured after the white noise pulse is emitted and used to determine a maximum degree of closure caused by the white noise pulse. This determined value may optionally be compared to a previous determination of inhibition, compared to a previous determination of closure following just the pulse (with no prepulse being emitted), or compared to a threshold value. In some embodiments, this determined value, and/or any comparison is transmitted 251, 253 to a remote device or server.

In some embodiments, the device is configured to perform only the eyeblink conditioning or the prepulse inhibition testing. In some embodiments, the device is configured to perform both.

In some embodiments, the device may be configured to utilize a virtual reality (VR)-type viewer (e.g., akin to a Google Cardboard® viewer) to prevent a substantial amount of outside light from reaching the eyes. For example, the housing may comprise or be connected to a flexible opaque polymer that surrounds the eyes and positions the camera and light source at an appropriate distance from the eyes to operate effectively.

Other Testing

As the above-described systems and methods already comprise the detection of eyes, other eye-related tracking aspects can be incorporated in the method or device.

In some embodiments, the one or more processors can also be configured to include eye position tracking. The eye position tracking includes the tracking of (i) fast eye movement (saccades and micro-saccades), (ii) smooth pursuit movements, and/or (iii) vestibulo-ocular movements. In preferred embodiments, if eye position tracking is utilized, the device is configured to utilize a VR-type viewer as described above.

In some embodiments, the one or more processors can also be configured to include pupil size tracking to measure the user's alertness during smartphone neurobehavioral testing. As is known in the art, pupil size decreases as alertness wanes. By analyzing captured images in order to measure the pupil diameter, and optionally normalizing them, the pupil size can be tracked over time in order to determine if the user is sufficiently alert. In some embodiments, a level of alertness is determined by comparison the pupil size to other pupil size measurements gathered during the user's testing. In some embodiments, a level of alertness is determined by comparing a measured pupil size to a threshold.

In some embodiments, the one or more processors can also be configured to include pupil size tracking to measure conditioned pupil responses. This is similar to eyeblink conditioning, but where the pupil size is measured instead of the eyelid position. That is, an image is captured containing the pupil, the pupil diameter is measured, and preferably normalized, after experiencing conditional and unconditional stimuli, just as is done using FEC for eyeblink conditioning.

In some embodiments, the one or more processors can also be configured to measure the conditioning of reaction time. As one example of this, a user will play a simple video game for a period of time, e.g., 5, minutes, 10 minutes, or 20 minutes. During the game, a cue will repeatedly appear on the screen. The user is instructed to tap the screen immediately after this cue appears. The app measures the user's reaction time, and the user will get feedback on his/her performance by showing the most recent and fastest reaction time on the screen. The user is motivated to improve (i.e., shorten) his/her reaction time. During the game, the background on the screen gradually changes color. A randomly selected color (for instance, purple) will always precede the appearance of the cue within a fixed time interval of, e.g., 100 milliseconds to 1 second. The user will not know this ahead of time. In Pavlovian terms, this selected color (purple, in this example) is the conditional stimulus (CS). The cue is the unconditional stimulus (US). The response is the unconditional response (UR). The finger tap in response to the CS after training is the conditioned response (CR). In one specific example, this game was tested with a little dragon (US) as a cue that appears at a sky that gradually changes color (CS).

Those skilled in the art will recognize or be able to ascertain using no more than routine experimentation many equivalents to the specific embodiments of the invention described herein. Such equivalents are intended to be encompassed by the following claims.

What is claimed is:

1. A device for eyeblink conditioning without air puffs, comprising one or more processors configured with instructions that, when executed, cause the one or more processors to:

at a first point in time, cause a speaker to start emitting a sound;

b. at a second point in time, cause a light source to start emitting light, where the second point in time follows the first point in time after a fixed delay interval;

c. at a third point in time, cause the speaker to stop emitting the sound and cause the light source to stop emitting light, the third point in time being after the second point in time;

d. receive one or more first images of at least one eye from a camera while the speaker is emitting a sound and the light source is not emitting light;

e. receive one or more second images of the at least one eye from the camera while the speaker is emitting a sound and the light source is emitting light; and f. determine a degree of openness of the at least one eye in each of the one or more first images and the one or more second images.

2. The device for eyeblink conditioning according to claim 1, wherein the one or more processors are within a mobile device.

3. The device for eyeblink conditioning according to claim 2, wherein the mobile device is a smartphone.

4. The device for eyeblink conditioning according to claim 1, further comprising a wireless transceiver.

5. The device for eyeblink conditioning according to claim 4, wherein the one or more processors are further configured to transmit the degree of openness to a remote device or server.

6. The device for eyeblink conditioning according to claim 4, wherein the one or more processors are further configured to transmit the one or more first images, the one or more second images, or a combination thereof, to a remote device or server.

7. The device for eyeblink conditioning according to claim 1, wherein the one or more processors are further configured to determine a degree to which a conditioned response is acquired, based on the determined degree of openness of the at least one eye in the one or more first images.

8. The device for eyeblink conditioning according to claim 1, wherein the fixed delay interval is between 100 milliseconds and 1 second.

9. The device for eyeblink conditioning according to claim 1, further comprising a vibration motor configured to start vibrating at the first point in time and stop vibrating at the third point in time.

10. The device for eyeblink conditioning according to claim 1, wherein the light source is a camera flash or a display screen.

11. The device for eyeblink conditioning according to claim 1, further comprising a display screen configured to display a video or image, an augmented reality video or image, or a virtual reality video or image.

12. The device for eyeblink conditioning according to claim 1, wherein the one or more processors are further configured to cause prepulse inhibition, by causing a white noise prepulse to be emitted, and after a delay period, causing a white noise pulse to be emitted, where a strength of the pulse is greater than a strength of the prepulse.

* * * * *